United States Patent [19]

Gaffney et al.

[11] Patent Number: 5,319,114
[45] Date of Patent: Jun. 7, 1994

[54] OLEFIN EPOXIDATION USING A CARBON MOLECULAR SIEVE IMPREGNATED WITH A TRANSITION METAL

[75] Inventors: Anne M. Gaffney, West Chester; Manish K. Nandi, Wayne; Rangasamy Pitchai; Yuan-Zhang Han, both of West Chester, all of Pa.

[73] Assignee: Arco Chemical Technology, L. P., Wilmington, Del.

[21] Appl. No.: 125,963

[22] Filed: Sep. 23, 1993

[51] Int. Cl.$^5$ .................. C07D 301/19; C07D 303/04
[52] U.S. Cl. ........................................................ 549/529
[58] Field of Search ............................................ 549/529

[56] References Cited

U.S. PATENT DOCUMENTS

| | | | |
|---|---|---|---|
| 3,259,638 | 7/1966 | Allison | 549/529 |
| 3,350,422 | 10/1967 | Kollar | 260/348.5 |
| 3,351,635 | 11/1967 | Kollar | 260/348.5 |
| 3,360,585 | 12/1967 | Winnick | 549/529 |
| 3,665,047 | 5/1972 | Gislon et al. | 549/529 |
| 3,947,500 | 3/1976 | Kollar | 549/529 |
| 4,593,012 | 6/1986 | Usui et al. | 502/167 |

FOREIGN PATENT DOCUMENTS

| | | |
|---|---|---|
| 0520779 | 12/1992 | European Pat. Off. |
| 0525974 | 2/1993 | European Pat. Off. |

OTHER PUBLICATIONS

"Carbonaceous Absorbents As Catalyst Supports", Russell S. Drago, Steven K. Showalter & Gerald C. Grunewald, American Chemical Society in Abstracts of Papers, Part 2, 206th ACS National Meeting, Aug. 22–27, 1993.
Chemical & Pharmaceutical Bulletin, vol. 33, No. 9, Sep. 1985 Itoi et al.
1985 The Chemical Society of Japan, Bull. Chem. Soc. Jpn. 58, 31933196 (1985) "Tungstic Acid–Tributyltin Chloride on a Charcoal Catalyst in the Epoxidation of Alkenes with Hydrogen Peroxide", Itoi et al.
Chem. Pharm. Bull 32(2) 418–423 (1984) "Epoxidation of Alkenes with Hydrogen Peroxide in the Presence of Molybdenum Oxide–Tributyltin Chloride on Charcoal Catalysts", Itoi et al.
Chemistry Letters pp. 1375–1378, 1982, "The Epoxidation of Olefins with Hydrogen Peroxide on Molybdenium Blue–Charcoal Catalysts", Inoue et al.
J. Am. Chem. Soc., 1991, 113, 1636–1639–"Carbon Molecular Sieves As Catalysts and Catalyst Supports", G. C. Grunewald & R. S. Drago.
Journal of Molecular Catalysis 7, (1980) 107–126, R. A. Sheldon, "Synthetic & Mechanistic Aspects of Metal–Catalysed Epoxidation with Hydroperoxides".

*Primary Examiner*—Joseph E. Evans
*Attorney, Agent, or Firm*—Stephen D. Harper

[57] ABSTRACT

Olefins are selectively converted to epoxides by reacting with an organic hydroperoxide in the presence of a heterogeneous catalyst comprised of a carbon molecular sieve containing a Group IVA, VA, VIA, or VIIA transition metal such as molybdenum.

20 Claims, No Drawings

OLEFIN EPOXIDATION USING A CARBON MOLECULAR SIEVE IMPREGNATED WITH A TRANSITION METAL

FIELD OF THE INVENTION

This invention relates to methods wherein an olefin may be selectively oxidized to an epoxide. More particularly, this invention pertains to catalytic epoxidation processes employing certain transition metals entrapped in a porous carbon matrix as catalyst and organic hydroperoxides as oxidizing agent.

BACKGROUND OF THE INVENTION

Epoxides such as ethylene oxide, propylene oxide, 1,2-butene oxide and the like are useful intermediates for the preparation of a wide variety of products. The oxirane functionality in such compounds is highly reactive and may be ring-opened with any number of nucleophilic reactants. For example, epoxides may be hydrolyzed to yield glycols useful as anti-freeze components, food additives, or reactive monomers for the preparation of condensation polymers such as polyesters.

Polyether polyols generated by the ring-opening polymerization of epoxides are widely utilized as intermediates in the preparation of polyurethane foams, elastomers, sealants, coatings, and the like. The reaction of epoxides with alcohols provides glycol ethers, which may be used as polar solvents in a number of applications.

Many different methods for the preparation of epoxides have been developed. One such method involves the epoxidation of an olefin in a liquid phase reaction using an organic hydroperoxide as the oxidizing agent and certain solubilized transition metal compounds as catalyst. The early work in this field concluded that optimum epoxidation rates and selectivity to epoxide generally are obtained using metallic catalysts which are soluble in an organic reaction medium. For example, U.S. Pat. No. 3,350,422 teaches in Example 6 that while vanadium naphthenate (a soluble catalyst) provided 72% hydroperoxide conversion and 38% selectivity to propylene oxide, vanadium pentoxide (an insoluble species) gave only 34% hydroperoxide conversion and 6% propylene oxide selectivity. Similarly, U.S. Pat. No. 3,351,635 teaches that metals such as molybdenum, tungsten and titanium are most effective as epoxidation catalysts when dissolved in the epoxidation reaction mixture. Poorly soluble species such as molybdenum trioxide thus are initially inactive and only become suitable for use in such application when converted to a soluble active form by reaction with alcohol, glycol, hydroperoxide or the like (see, for example, the discussion in Sheldon, J. Mol. Cat. 7, pp. 107-126 (1980)).

A distinct disadvantage of an epoxidation process which utilizes a soluble metallic compound as catalyst is the difficulty associated with recovering the catalyst for reuse in subsequent runs. When the other components of an epoxidation reaction mixture (typically, epoxide, unreacted olefin, solvent, unreacted hydroperoxide, and the alcohol derived from the reacted hydroperoxide) are relatively volatile, these components may be separated from the soluble non-volatile catalyst by distillation and the catalyst recovered in the form of a bottoms stream. A problem associated with such a method, however, is that the bottoms stream may tend to accumulate certain heavy substances such as acids and polymers which may have a deleterious effect on epoxide selectivity or olefin conversion when the stream is reused. The catalyst may also have a tendency to precipitate from solution if the bottoms stream is overly concentrated; recycle of a relatively large bottoms stream may thus be required, which will detrimentally affect the productivity of the epoxidation process. It would therefore be highly desirable to develop an insoluble (heterogeneous) epoxidation catalyst which has high activity and selectivity and which may be readily recovered in active form from an epoxidation reaction mixture by filtration or similar separation techniques or which may be utilized in the form of a fixed bed or the like.

SUMMARY OF THE INVENTION

This invention provides a process for producing an epoxide comprising contacting an olefin with an organic hydroperoxide and a catalytic amount of a carbon molecular sieve impregnated with a Group IVA, VA, VIA, or VIIA transition metal such as titanium, tungsten, chromium, vanadium, molybdenum, nickel, or rhenium for a time and at a temperature effective to convert the olefin to the epoxide.

In a particular embodiment, the invention furnishes a method for forming an epoxide comprising contacting a $C_2$-$C_{10}$ olefin with an organic hydroperoxide having the general structure

wherein $R^1$, $R^2$, $R^3$ are the same or different and are selected from hydrogen, $C_1$-$C_6$ alkyl, and aryl provided that a maximum of one of $R^1$, $R^2$, and $R^3$ is hydrogen, and a catalytic amount of a carbon molecular sieve having an average pore radius of from 1 to 100 angstroms and a surface area of at least 100 m$^2$/g and impregnated with from 1 to 20 weight percent of molybdenum at a temperature of from 50° C. to 150° C. for a time effective to convert the olefin to the epoxide.

A distinct advantage of the present invention is that the catalyst employed is heterogeneous and thus may be readily recovered or separated from an epoxidation reaction mixture and reused. Additionally, the catalysts utilized in the process of this invention, despite their insoluble character, have good activity and transform olefins into epoxide in a highly selective manner.

DETAILED DESCRIPTION OF THE INVENTION

The catalyst used in the process of this invention is a carbon molecular sieve containing transition metal atoms on its external surface and/or within its pores. Although the precise mechanism is not known, the transition metal atoms are apparently trapped or immobilized inside the carbon molecular sieve matrix in a manner such that the transition metal atoms are not readily solubilized and yet are available for interaction with the olefin and the hydroperoxide, thereby facilitating the catalytic transfer of oxygen from the hydroperoxide to the olefin to form the desired epoxide.

Carbon molecular sieves suitable for use in preparing the metal-containing catalysts are well known in the art and are amorphous materials with average pore dimensions similar to the critical dimensions of individual molecules. These carbon-based absorbents have also been referred to as ultra microporous carbons and contain a large specific pore volume primarily in pores of molecular dimensions. They are generally obtained by the controlled pyrolysis of natural and synthetic precursors, including coal, coconut shells, pitch, phenolformaldehyde resins, styrene-vinyl benzene sulfonated resins, polyfurfuryl alcohol, polyacrylonitrile, and polyvinylidene chloride. Suitable precursors may be cross-linked and may contain a cation, anion, strong base, weak base, sulfonic acid, carboxylic acid, halogen, or alkyl amine functionality. The chemistry of such materials is reviewed, for example, in Foley, "Carbon Molecular Sieves Properties and Applications in Perspective", in *Perspectives in Molecular Sieve Science*, Flank et al., Eds., American Chemical Society, pp. 335-360 (1988), Schmitt, "Carbon Molecular Sieves as Selective Catalyst Supports-10 Years Later", *Carbon*, 29(6) pp. 743-745 (1991), and Walker, "Carbon-An Old But New Material Revisited", *Carbon*, 28(2/3), pp. 261-279 (1990). Certain carbon molecular sieves are available from commercial sources and may also be utilized as starting materials for the catalysts employed in the process described herein. Such carbon molecular sieves include, for example, the Ambersorb series of absorbent offered by the Rohm and Haas Company (e.g., "Ambersorb 563", "Ambersorb 564", "Ambersorb 572", "Ambersorb 575", "Ambersorb 348F") as well as the carbon molecular sieve materials available from Anderson Development Company ("Type AX21"), Calgon Carbon Corporation ("Calgon MSC-V"), Alltech Associates ("Carbosphere"), and Takeda ("5A Carbon"). References describing methods of preparing carbon molecular sieves include Lafyatis et al., *Ind. Eng. Chem. Res.* 30, pp. 865-873 (1991), Japanese Kokai No. 61-191,510 (abstracted in *Chem. Abst.* 105: 229264y), U.S. Pat. No. 4,082,694 (Wennerberg et al.), U.S. Pat. No. 4,839,331 (Maroldo et al.), U.S. Pat. No. 4,040,990 (Neely), and U.S. Pat. No. 4,528,281 (Sutt) among others; the teachings of these publications are incorporated herein by reference in their entirety.

The Group IVA, VA, VIA, or VIIA transition metal entrapped in the carbon molecular sieve may preferably be selected from titanium, tungsten, chromium, vanadium, nickel, rhenium, or, most preferably, molybdenum. Mixtures or combinations of different transition metals may also be employed. The precise form of the transition metal present in the carbon molecular sieve is not critical to the successful operation of the process of this invention, but the oxidation state of the metal and the substituents or ligands bound to or otherwise associated with the transition metal should be such as to permit the metal center to participate in the transfer of an oxygen atom from the organic hydroperoxide to the olefin. Metal oxides represent an exemplary class which may suitably be utilized. Transition metal-doped carbon molecular sieves of this type are known in the art and may be obtained by any of the synthetic procedures taught in the following publications among others (all of which are incorporated by reference in their entirety): European Pat. Pub Nos. 520,779 and 525,974, U.S. Pat. Nos. 4,447,665 (Wennerberg), 4,482,641 (Wennerberg), 4,518,488 (Wennerberg), 4,569,924 (Ozin et al.), 4,591,578 (Foley et al.), 4,656,153 (Wennerberg), 4,970,189 (Tachibana), 4,992,404 (Gruhl et al.), and 5,051,389 (Lang et al.), Canadian Pat. Appl. No. 2,047,080, and Grunewald et al., "Carbon Molecular Sieves as Catalysts and Catalyst Supports", *J. Am. Chem. Soc.* 113, pp. 1636-1639 (1991).

The physical and chemical characteristics of the carbon molecular sieve may be manipulated as desired in order to favorably influence the activity and selectivity of the resulting catalyst when utilized to epoxidize olefins in the process of this invention. Such characteristics include, for example, surface area, average pore radius, distribution of pore sizes, pore volume (including the relative macropore, mesopore, and micropore volumes), acidity/basicity, hydrophobicity/hydrophilicity, and the like. The optimum type of carbon molecular sieve for a particular epoxidation application will vary depending upon the choice of olefin and organic hydroperoxide, transition metal, reaction conditions, reaction medium (solvent), and so forth. For example, the particular size and shape of the olefin to be epoxidized and the organic hydroperoxide serving as the source of oxygen will affect the selection of the carbon molecular sieve best suited for the process of this invention. Such optimization may be readily performed by the worker of ordinary skill in the art using routine experimental methods.

Generally speaking, the transition metal content of the carbon molecular sieve is not critical and may be varied within wide limits. Sufficient metal should be incorporated so as to avoid the need to utilize an excessively large amount of the doped carbon molecular sieve relative to the volume of organic reactants, but the metal concentration should not be so high that leaching of the metal into solution becomes a problem. Typically, the carbon molecular sieve may contain from 0.01 to 25 percent by weight (preferably, from 1 to 20 percent by weight) of the transition metal. In general, higher loadings of transition metal are possible by increasing the surface area of the carbon molecular sieve. Sufficient metal-impregnated carbon molecular sieve is present in the reaction zone together with the olefin and organic hydroperoxide to attain a practically rapid rate of epoxidation. The optimum amount of the catalyst will, of course, depend on a number of variables including temperature, the relative reactivities and concentrations of olefin and hydroperoxide, the identity and activity of the transition metal selected, and so forth, but generally the catalyst is present at a concentration sufficient to provide from 10 to 10,000 ppm transition metal based on the combined weight of olefin and organic hydroperoxide.

The average pore radius of the carbon molecular sieve may be altered as desired, but usually will advantageously be in the range of from 1 to 100 angstroms although larger average pore sizes may also be useful under certain conditions. The relative proportions of macropores (>500 angstroms), mesopores (20-500 angstroms), and micropores (<20 angstroms) may be manipulated as needed to attain maximum catalyst productivity with regard to the desired epoxide product. The carbon molecular sieve can possess any surface area provided the resulting doped catalyst is active in the epoxidation reaction. Generally, the carbon molecular sieve possesses a surface area of at least about 100 m$^2$/g with a surface area of at least 500 m$^2$/g being advantageous in certain epoxidation applications. The surface area may be as high as the theoretical maximum possible for such substances; the surface area thus, for example, may be as high as 2000-3000 m$^2$/g. In order to avoid problems with ring-opening reactions of the epoxide product, the carbon molecular sieve containing the transition metal is preferably not highly acidic.

The transition metal-containing carbon molecular sieve may be employed in any suitable physical form, including powders, particles, beads, pellets, monoliths, spheres, granules, blocks, saddles, extrudates, and the like. Preferably, the carbon molecular sieve is sufficiently hard to resist attrition or other physical degradation during practice of the instant process, particularly when the process is carried out on a continuous basis for an extended period of time.

The organic hydroperoxide to be used as the oxidizing agent in the process of this invention may be any organic compound having at least one hydroperoxy functional group (-OOH). Secondary and tertiary hydroperoxides are preferred, however, owing to the higher instability and greater safety hazards associated with primary hydroperoxides. The organic hydroperoxide preferably has the general structure

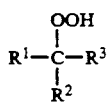

wherein $R^1$, $R^2$, and $R^3$ are the same or different and are selected from the group consisting of hydrogen, $C_1$–$C_6$ alkyl, and aryl. Preferably, the R groups are selected from hydrogen, methyl, ethyl, and phenyl wherein a maximum of one R group is hydrogen. The aforementioned R groups may each be a substituted or unsubstituted alkyl, cycloalkyl, aralkyl, aralkenyl, hydroxyaralkyl, cycloalkenyl, hydroxycycloalkyl and the like having from one to 10 carbon atoms. The hydroxy hydroperoxy species formed by the air oxidation of alcohols such as cyclohexanol may also be employed. Exemplary hydroperoxides include t-butyl hydroperoxide, t-amyl hydroperoxide, cumene hydroperoxide, ethyl benzene hydroperoxide, cyclohexane hydroperoxide, methyl cyclohexane hydroperoxide, tetralin hydroperoxide, isobutyl benzene hydroperoxide, isopropyl hydroperoxide, ethyl naphthalene hydroperoxide, tetralin hydroperoxide, and the like. Mixtures of organic hydroperoxides may also be employed. The amount of organic hydroperoxide is not critical, but most suitably the molar ratio of olefin:organic hydroperoxide is from about 100:1 to 1:100 when the olefin contains one ethylenically unsaturated group. The molar ratio of ethylenically unsaturated groups in the olefin substrate to organic hydroperoxide is more preferably in the range of from 20:1 to 1:5. One equivalent of hydroperoxide is theoretically required to oxidize one equivalent of a mono-unsaturated olefin substrate, but it may be desirable to employ an excess of one reactant to optimize selectivity to the epoxide.

The olefin substrate may be any organic compound having at least one ethylenically unsaturated functional group (i.e., a carbon-carbon double bond) and may be an aromatic, aliphatic, mixed aromatic-aliphatic (e.g., aralkyl), cyclic, branched or straight chain olefin. Preferably, the olefin contains from 2 to 30 carbon atoms (i.e., a $C_2$–$C_{30}$ olefin). Olefins containing from two to ten carbon atoms are especially preferred. The olefinic double bond may be in a terminal or internal position on the olefin or may form part of a cyclic structure as a cyclohexene. More than one carbon-carbon double bond may be present in the olefin; dienes, trienes, and other polyunsaturated substrates thus may be used.

Other examples of suitable substrates include unsaturated fatty acids or fatty acid derivatives such as esters or glycerides and oligomeric or polymeric unsaturated compounds such as polybutadiene.

In one embodiment, the olefin is a $C_2$–$C_{30}$ olefin having the general structure

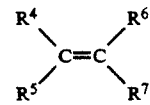

wherein $R^4$, $R^5$, $R^6$, and $R^7$ are the same or different and are selected from hydrogen, $C_1$–$C_{20}$ alkyl, $C_7$–$C_{20}$ aryl alkyl, $C_5$–$C_{20}$ alkyl cycloalkyl, and $C_6$–$C_{20}$ aryl.

The olefin may contain substituents other than hydrocarbon substituents such as halide, carboxylic acid, ether, hydroxy, thiol, nitro, cyano, ketone, ester, anhydride, amino, and the like, provided such substituents do not interfere with the desired epoxidation reaction.

Exemplary olefins suitable for use in the process of this invention include ethylene, propylene, the butenes such as 1-butene, 2-butene and isobutylene, butadiene, the pentenes such as 1-pentene and 2-pentene, isoprene, 1-hexene, 1-octene, diisobutylene, 1-nonene, 1-tetradecene, pentamyrcene, camphene, 1-undecene, 1-dodecene, 1-tridecene, 1-tetradecene, 1-pentadecene, 1-hexadecene, 1-heptadecene, 1-octadecene, 1-nonadecene, 1-eicosene, the trimers and tetramers of propylene, polybutadiene, polyisoprene, cyclopentene, cyclohexene, cycloheptene, cyclooctene, cyclooctadiene, cyclododecene, cyclododecatriene, dicyclopentadiene, methylenecyclopropane, methylenecyclopentane, styrene (and other styrenic substrates), methylenecyclohexane, vinylcyclohexane, vinyl cyclohexene, methallyl alcohol, allyl alcohol, allyl chloride, allyl bromide, allyl phenyl ether, allyl ethyl ether, acrylic acid, methacrylic acid, crotonic acid, vinyl acetic acid, crotyl chloride, methallyl chloride, the dichlorobutenes, allyl carbonate, allyl acetate, allyl acrylates and methacrylates, diallyl maleate, diallyl phthalate, unsaturated triglycerides such as soybean oil, and unsaturated fatty acids, such as oleic acid, linolenic acid, linoleic acid, erucic acid, oleosteric acid, myristic acid, palmitic acid, and ricinoleic acid and their esters.

An organic solvent or mixture of organic solvents may additionally be present when the olefin is contacted with the hydroperoxide and catalyst. Alternatively, the desired reaction may be conducted in a neat state (without solvent) or using an excess of one reactant such as the olefin as a diluent. The solvent may be used to dilute, disperse, or dissolve the components of the reaction mixture, thus providing better temperature control or faster reaction rates. The identity of the solvent may advantageously be altered to control the rate or selectivity of the epoxidation process. Examples of suitable organic solvents include, but are not limited to, aliphatic hydrocarbons (e.g., hexane, cyclohexane, petroleum ether), aromatic hydrocarbons (e.g., benzene, toluene, xylene, ethyl benzene, napthalene, cumene), and halogenated hydrocarbons (e.g., methylene chloride, chloroform, carbon tetrachloride, trichloroethane, chlorobenzene). The amount of organic solvent is not critical, but typically will be from about 5 to 95 weight % of the total reaction mixture. It is generally desirable to carry out the process of this invention under an inert atmosphere, that is, in the absence of oxygen.

In one embodiment of the invention, the solvent is a hydrocarbon or alcohol which corresponds in carbon skeleton to the organic hydroperoxide being used as the oxidant. For example, when tertiary butyl hydroperoxide is employed as the organic hydroperoxide, tertiary butyl alcohol may be used as solvent. Similarly, when ethyl benzene hydroperoxide is the oxidant, the solvent may be ethyl benzene. Mixtures of hydroperoxides and their corresponding alcohols or hydrocarbons may be readily generated by air oxidation of a hydrocarbon such as isobutane or ethyl benzene.

The reaction temperature is not critical, but should be sufficient to accomplish substantial conversion of the olefin to epoxide within a reasonably short period of time. It is generally advantageous to carry out the reaction to achieve as high a hydroperoxide conversion as possible, preferably at least 50% and desirably at least 90%, consistent with reasonable selectivities. The optimum reaction temperature will be influenced by catalyst activity, olefin reactivity, reactant concentrations, and type of solvent employed, among other factors, but typically will be in a range of from about 50° C. to 150° C. More preferably, the temperature will be from about 70° C. to 125° C. Reaction or residence times of from about 1 minute to 48 hours (more preferably, 10 minutes to 3 hours) will typically be appropriate, depending upon the above-identified variables. Although subatmospheric pressures can be employed, the reaction is preferably performed at atmospheric pressure or at elevated pressure (typically, not greater than about 2,000 psig). Generally, it will be desirable to maintain the reaction components as a liquid phase mixture.

The process of this invention may be carried out in a batch, continuous, or semi-continuous manner using any appropriate type of reaction vessel or apparatus. The reactor advantageously may be a fluidized bed, fixed bed, transport bed, moving bed, continuous stirred tank (CSTR), or stirred slurry reactor. Known methods for conducting transition metal catalyzed epoxidations of olefins using organic hydroperoxides will generally also be suitable for use in this process. Thus, the reactants may be combined all at once or sequentially. For example, the organic hydroperoxide may be added incrementally to the reaction zone. In one embodiment of the process, the olefin and organic hydroperoxide are introduced separately or as a mixture into a reaction zone wherein the catalyst is maintained in solid form as a fixed, mobile, fluidized or moving bed. As the olefin and hydroperoxide pass over and come into contact with the catalyst, the desired epoxide product is formed and may be withdrawn from the reaction zone as a liquid stream together with the alcohol derived from the reacted hydroperoxide. Once the epoxidation has been carried out to the desired degree of conversion, the desired epoxide product may be separated and recovered from the reaction mixture using any appropriate technique such as fractional distillation, extractive distillation, liquid-liquid extraction, crystallization, or the like. The co-product of the reaction will generally be the corresponding alcohol derived from the organic hydroperoxide and may similarly be separated and recovered for use as a valuable product in its own right. For example, t-butyl alcohol will be produced if t-butyl hydroperoxide is employed as the oxidant while methyl benzyl alcohol is obtained using ethyl benzene hydroperoxide. The alcohol product can in turn be readily dehydrated to a useful olefin such as isobutylene or styrene. These olefins may, if desired, be hydrogenated and then oxidized to the organic hydroperoxide. After separation from the epoxidation reaction mixture, the recovered transition metal-doped carbon molecular sieve catalyst may be economically re-used in subsequent epoxidations. Periodic reactivation or regeneration of the catalyst may be advantageous. Any unreacted olefin or organic hydroperoxide may also be separated and recycled.

From the foregoing description, one skilled in the art can readily ascertain the essential characteristics of this invention, and, without departing from the spirit and scope thereof, can make various changes and modifications of the invention to adapt it to various usages, conditions, and embodiments.

The following examples further illustrate the process of this invention, but are not limitative of the invention in any manner whatsoever.

EXAMPLES

EXAMPLE 1

A carbon molecular sieve impregnated with molybdenum was prepared by refluxing "Ambersorb 348F" absorbent (2.5 g; obtained from the Rohm and Haas Company; this carbon molecular sieve has a surface area of 750 $m^2/g$, a microporosity of 0.32 mL/g, a mesoporosity of 0.12 mL/g, and a macroporosity of 0.13 mL/g.) together with molybedum trioxide (0.45 g) in water (50 mL) for six hours. The water was removed by rotary evaporation. The catalyst thus obtained was subsequently dried at 100° C. under vacuum.

To demonstrate the utility of the Mo-entrapped carbon molecular sieve prepared as described herein above as an epoxidation catalyst, a series of runs were performed wherein a stirred reactor flask was charged with catalyst (ca. 0.5 g), 1-octene (25 g), and tertiary butyl hydroperoxide (either 5.9 g of an oxidate mixture obtained by air oxidation of isobutane containing ca. 40% TBHP in tertiary butyl alcohol or 2.5 g of 90% tertiary butyl hydroperoxide obtained from Aldrich Chemical containing ca. 5% water and ca. 5% tertiary butyl alcohol). Decane (ca. 1.2 g) was also added to provide an internal standard. The mixture was heated to 90° C. under a nitrogen atmosphere and small samples of the reaction mixture removed and analyzed after 4 hours. After an initial conditioning run (wherein most of the molybdenum not entrapped by the carbon molecular sieve was dissolved into the reaction mixture), a series of epoxidations using the same catalyst sample was performed. In each case, the liquid reaction mixture was drained from the catalyst and a fresh charge of reactants having the same composition described above for the conditioning run was charged to the reaction flask.

The results obtained are shown in Tables I and II.

TABLE I

| Run # | 1* | 2 | 3 | 4 |
|---|---|---|---|---|
| TBHP Conversion, % | 98.7 | 75.4 | 64.8 | 58.6 |
| Epoxide Selectivity (based on TBHP, converted), % | 70.0 | 78.6 | 77.6 | 81.3 |
| Soluble Mo, ppm | 140 | 5 | <0.8 | 0.8 |

*conditioning run

The carbon molecular sieve used in these runs contained 7.2 wt % Mo both when fresh and after recovery, indicating that the amount of molybdenum lost through solubilization was negligible. These runs used 90% TBHP.

TABLE II

| Run # | 1* | 2 | 3 | 4 | 5 |
| --- | --- | --- | --- | --- | --- |
| TBHP Conversion, % | 97.0 | 98.5 | 82.4 | 76.0 | 64.9 |
| Epoxide Selectivity (based on TBHP converted), % | 80.7 | 85.2 | 84.3 | 80.2 | 85.3 |
| Soluble Mo, ppm | 150 | 56 | 9.5 | 4.1 | 4.3 |

*conditioning run

The carbon molecular sieve recovered from these runs contained 6.8 wt % Mo. These runs used an oxidate mixture containing ca. 40% TBHP in tertiary butyl alcohol.

EXAMPLE 2

A catalyst is prepared by placing 2.5 g of Anderson AX21 carbon molecular sieve (dried under vacuum at 100° C. for 8 hours) in a round bottom flask together with 50 ml deionized water. The mixture is stirred and 0.5 g tungsten trioxide ($WO_3$) is added to the flask. The resulting mixture is refluxed for 6 hours. Excess water is removed by rotary evaporation and the tungsten-doped carbon molecular sieve dried at 100° C. for 8 hours.

The resulting catalyst is utilized in the epoxidation of cyclohexene to cyclohexene oxide using ethyl benzene hydroperoxide as oxidant at a temperature of 100° C.

EXAMPLE 3

A titanium doped catalyst is obtained by adding 6.0 mL of 1.0M titanium tetrachloride in dichloromethane to 4.06 g of "Ambersorb 572" carbon molecular sieve (available from the Rohm and Hass Company) under a blanket of nitrogen. The solvent is removed under vacuum at room temperature (14 hours). Hydrolysis of the metal species present to titanium dioxide is accomplished by exposure to atmospheric water vapor. The resulting carbon molecular sieve having titanium oxide entrapped within is used to epoxidize propylene at a reaction temperature of 110° C.; cumene hydroperoxide is used as the organic hydroperoxide (0.8 moles per mole of propylene). Propylene oxide is the expected major product.

EXAMPLE 4

A vanadium-carbon-based catalyst prepared as described in Example 1 of U.S. Pat. No. 4,992,404 (Gruhl et al.) is contacted with allyl alcohol and tertiary amyl hydroperoxide at 50° C. to form glycidol as the expected epoxidation product.

The above-described examples confirm that the process of this invention usefully converts olefins to epoxides and that the catalyst utilized may be easily recovered and used again in subsequent epoxidation reactions with little or no loss in selectivity.

We claim:

1. A process for producing an epoxide comprising contacting an olefin with an organic hydroperoxide in the presence of a catalytic amount of a carbon molecular sieve impregnated with a Group IVA, VA, VIA, or VIIA transition metal for a time and at a temperature effective to convert the olefin to the epoxide.

2. The process of claim 1 wherein the transition metal is molybdenum, titanium, tungsten, or vanadium.

3. The process of claim 1 wherein said contacting is carried out in a liquid phase.

4. The process of claim 1 wherein the temperature is from 50° C. to 150° C.

5. The process of claim 1 wherein the organic hydroperoxide is selected from tertiary butyl hydroperoxide, tertiary amyl hydroperoxide, cumene hydroperoxide, ethyl benzene hydroperoxide, cyclohexyl hydroperoxide, and methyl cyclohexyl hydroperoxide.

6. The process of claim 1 wherein the olefin is a $C_2$–$C_{30}$ olefin having the general formula

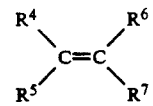

wherein $R^4, R^5, R^6$, and $R^7$ are the same or different and are selected from hydrogen, $C_1$–$C_{20}$ alkyl, $C_7$–$C_{20}$ aryl alkyl, $C_5$–$C_{20}$ alkyl cycloalkyl, and $C_6$–$C_{20}$ aryl.

7. The process of claim 1 wherein the olefin is selected from the group consisting of ethylene, propylene, 1-butene, 2-butene, 1-pentene, 2-pentene, 1-octene, allyl alcohol, allyl chloride, methallyl alcohol, methallyl chloride, styrene, cyclohexane, cyclooctene, allyl phenyl ether, norbornene, isoprene, butadiene, isobutylene, and vinyl cyclohexane.

8. The process of claim 1 wherein the carbon molecular sieve contains from 0.01 to 25 percent by weight of the transition metal.

9. The process of claim 1 wherein the carbon molecular sieve has an average pore radius of from 1 to 100 angstroms.

10. The process of claim 1 wherein the carbon molecular sieve has a surface area of greater than 100 $m^2/g$.

11. The process of claim 1 wherein the molar ratio of olefin: organic hydroperoxide is from 20:1 to 1:5.

12. The process of claim 1 wherein the carbon molecular sieve is present at a concentration sufficient to provide from 10 to 10,000 ppm transition metal based on the combined amount of olefin and organic hydroperoxide.

13. The process of claim 1 wherein an organic solvent is additionally present during said contacting.

14. The process of claim 13 wherein the organic solvent is an alcohol or hydrocarbon corresponding in carbon skeleton to the organic hydroperoxide.

15. A process for producing an epoxide comprising contacting a $C_2$–$C_{10}$ olefin with an organic hydroperoxide having the general structure

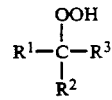

wherein $R^1, R^2$, and $R^3$ are the same or different and are selected from hydrogen, $C_1$–$C_6$ alkyl, and aryl provided that a maximum of one of $R^1$, $R^2$, and $R^3$ is hydrogen, and a catalytic amount of a carbon molecular sieve having an average pore radius of from 1 to 100 angstroms and a surface area of at least 100 $m^2/g$ and impregnated with from 1 to 20 weight percent of molybdenum at a temperature of from 50° to 150° C. for a time effective to convert the olefin to the epoxide.

16. The process of claim 15 wherein the olefin is selected from ethylene, propylene, 1-butene, 2-butene, isobutylene, 1-pentene, 2-pentene, 1-octene, allyl alcohol, methallyl alcohol, styrene, cyclohexene, cyclooctene, allyl phenyl ether, allyl ethyl ether, norbornene, isoprene, butadiene, and vinyl cyclohexane.

17. The process of claim 15 wherein the organic hydroperoxide is selected from tertiary butyl hydroperoxide, tertiary amyl hydroperoxide, cumene hydroperoxide, ethyl benzene hydroperoxide, cyclohexyl hydroperoxide, and methyl cyclohexyl hydroperoxide.

18. The process of claim 15 wherein the olefin is propylene and the organic hydroperoxide is tertiary butyl hydroperoxide or ethyl benzene hydroperoxide.

19. The process of claim 15 wherein the organic hydroperoxide is generated by air oxidation of a hydrocarbon corresponding in carbon skeleton to the organic hydroperoxide.

20. The process of claim 15 wherein the organic hydroperoxide is converted to an alcohol corresponding in carbon skeleton to the organic hydroperoxide during said contacting.

* * * * *